United States Patent [19]

Clark et al.

[11] Patent Number: 4,753,747

[45] Date of Patent: Jun. 28, 1988

[54] PROCESS OF NEUTRALIZING MONO-CARBOXYLIC ACID

[75] Inventors: Kenneth F. Clark, Hazlet; Remo J. Colarusso, Jr., Somerset; Barry Weinstein, North Brunswick, all of N.J.

[73] Assignee: Colgate-Palmolive Co., New York, N.Y.

[21] Appl. No.: 49,760

[22] Filed: May 12, 1987

[51] Int. Cl.$^4$ ................... C11D 17/08; C11D 13/00
[52] U.S. Cl. ......................................... 252/90; 252/108; 252/117; 252/118; 252/132; 260/417
[58] Field of Search ............... 260/417; 252/108, 117, 252/118, 132

[56] References Cited

U.S. PATENT DOCUMENTS 3,541,581 11/1967 Monson .............................. 252/90

*Primary Examiner*—Prince E. Willis
*Assistant Examiner*—Isabelle Rodriguez
*Attorney, Agent, or Firm*—Richard N. Miller; Murray M. Grill; Richard J. Ancel

[57] ABSTRACT

The present invention relates to a process for making liquid soap, preferably without the need for melting the fatty acid and most preferably without the need for external heating or cooling and to the use of said process in making soap-containing cosmetic products, particularly shave cream in either aerosol or post foaming gel form.

19 Claims, No Drawings

PROCESS OF NEUTRALIZING MONO-CARBOXYLIC ACID

BACKGROUND OF THE INVENTION

Most of the liquid soaps today are made by one of two basic methods. In the first method, molten neutral fats or oils comprising triglycerides are reacted with a neutralizing agent in either a batch or continuous process to form a soap, with glycerine being recovered as a by product. Batch processes which have been employed to manufacture soap by this method include the kettle or full boiled process, the semiboiled process, the cold process and the autoclave process; and continuous processes for practicing this method include the Sharples process and the Mon Savon process. However, all of these processes are characterized by neutralization of molten or liquid fats and oils.

In the second method, fatty acids obtained by splitting or hydrolysis of natural fats and oils are neutralized with a suitable neutralizing agent in either a batch or continuous process. Again, the fatty acid typically is employed in molten or liquid form. Use of molten fatty acids requires application of heat to melt the various fatty acids which, with the exception of oleic acid (m.p. of 14° C.) and the coconut fatty acid mixture obtained from coconut oil (m.p. of 25.4° C.), are solids at room temperature, i.e., 21° C. to 25° C. For example, the melting points of various $C_{12}$–$C_{18}$ fatty acids follows: lauric acid-47° C.; myristic acid-54° C.; palmitic acid-62° C.; stearic acid-69° C.; and tallow fatty acid-40°–45° C.

Because the foregoing processes utilize significant amounts of energy, various proposals have been made to produce soap using reduced amounts of energy. For example, U.S. Pat. No. 1,722,687 discloses a process for manufacturing a dry soap powder comprising reacting an emulsion of 46% by weight of palm kernel fatty acids in water having a temperature of 50° C. with a particulate soda ash in a pinned disc mill to form a soap powder. U.S. Pat. No. 2,730,539 discloses a process for the manufacture of soap without addition of external heat by reacting molten tallow at 100° C. with a 50% sodium hydroxide solution in a Muller mixer for two and one half hours to produce a soap wherein saponification was completed overnight. U.S. Pat. No. 4,336,203 also discloses a process for producing soap wherein liquid fatty acid and 50% sodium hydroxide are reacted at 50° C. in the high shear field of a rotor-stator machine to produce a soap having a moisture content of about 15% by weight. Similarly. U.S. Pat. No. 4,376,079 discloses a process for making a soap containing 20% to 50% moisture by reacting a dispersion of metal oxide or hydroxide with an emulsion of fatty acid in water. U.S. Pat. No. 2,578,366, too, discloses a process for making soap containing 19-25% by weight of water comprising mixing solid fatty acid crystals dispersed in a melt of liquid fatty acid with a sodium hydroxide solution at 54° C. to 100° C. However, the energy saving accomplished by the foregoing processes is based upon the elimination of the heat required for drying the resultant soap rather than by eliminating the heat required for melting the fatty acid.

Based upon the foregoing discussion, it is apparent that there is a need for a process of making liquid soap for use in the manufacture of cosmetic products, e.g., shaving cream, skin lotions, etc., wherein energy can be conserved by omitting the need for energy input to melt the fatty acids and, preferably, by omitting the need for use of external cooling to reduce the temperature of either the soap or the ultimate cosmetic product.

SUMMARY OF THE INVENTION

The present invention broadly relates to a more energy efficient process for making a liquid, water soluble aqueous soap solution containing from about 0.3% by weight to about 40% by weight of neutralized soap which comprises the step of contacting finely divided particles of $C_{10}$–$C_{22}$ carboxylic acid with a neutralizing agent in an aqueous medium at a temperature below the melting point of the carboxylic acid, said carboxylic acid having a particle size less than about 2000 microns which is sufficient to form a neutralized soap which is free of carboxylic acid particles upon reaction with a substantially equimolar quantity of a neutralizing agent and recovering said liquid soap solution. Such process has the specific advantage of making a soap without the need for first melting the reactant fatty acid.

In a more preferred aspect, the inventive process comprises the steps of (A) forming an aqueous dispersion of a $C_{12}$–$C_{18}$ fatty acid having a particle size such that about 99% by weight is less than 420 microns and at least about 90% by weight is less than 177 microns by either dispersing a particulate fatty acid of said size in water or by wet grinding an aqueous dispersion of particulate fatty acid to said particle size and (B) neutralizing said aqueous dispersion with said neutralizing agent which is preferably mono-, di- or triethanolamine to form a liquid soap solution containing from 4% by weight to 30% by weight of alkanolamine soap, said steps A and B being carried out at a temperature of from 4° C. to about 43° C. which is below the melting point of the particulate fatty acid. This preferred process is particularly energy efficient because it can be carried out either without significant heating or at essentially room temperature in the absence of either external heating and/or external cooling.

Furthermore, the inventive process is particularly useful in preparing cosmetic formulations, e.g., aerosol and post-foaming gel shaving cream, shampoos, hair treating compositions, etc., which contain a water-soluble soap as an essential ingredient. More specifically, each of the essential process steps optionally can be carried out in the presence of other ingredients which are normally present in the ultimate cosmetic composition and, thus, said process offers a great degree of flexibility to the formulator. In fact, practice of the inventive process in the presence of such optional ingredients results in advantages in the method of manufacturing the cosmetic compositions. For example, when the inventive process is used in the manufacture of post-foaming gel shave cream, the presence of a surfactant in the step of forming the aqueous carboxylic acid dispersion facilitates the formation of a more stable dispersion of carboxylic acid which in turn is effective to form a readily pumpable and substantially stable, homogeneous dispersion of said agent in the final shave cream product. In addition, the inventive process is advantageous in preparing an aerosol shave cream composition which does not require melting the fatty acid and is very effective in forming a shampoo containing water soluble soap as a conditioning ingredient simply by admixing the aqueous dispersion of fatty acid in the balance of the formulation, including the neutralizing agent, to form a liquid soap in situ.

DETAILED DESCRIPTION OF THE INVENTION

The carboxylic acid employed in the inventive process can be either a saturated or unsaturated mono-carboxylic acid having a melting point above about 21° C.–25° C. and a carbon chain of about 10 to 22 carbons, with carbon chains of 12 to 18 carbon atoms being preferred, as well as a mixture of two or more of these acids. Such carboxylic acids can be derived from natural sources, e.g., fats and oils, or can be made by chemical synthesis, with the naturally derived fatty acids being most commonly used and preferred. Acids suitable for use in this invention include lauric acid, myristic acid, palmitic acid, hydrogenated tallow fatty acids, coconut oil fatty acids, behenic acid, ricinoleic acid, hydroxy stearic acid and mixtures of any of the foregoing acids. Such acids are well known articles of commerce and are often used in the form of mixtures such as lauric-myristic acids and commercial palmitic and stearic acids. The preferred acids vary according to the nature of the final cosmetic product, with palmitic acid and stearic acid or mixtures thereof being preferred for shaving cream compositions.

The preferred water-soluble soaps produced by the inventive process include mono, di- and triethanolammonium soaps and mixtures of the foregoing. Such soaps are obtained usually by reacting the organic carboxylic acid with the appropriate ethanolamine. The ethanolamine soaps, particularly triethanolamine soaps, are preferred because such soaps are readily soluble or pumpable in water at concentrations up to 40% by weight at 23° C. Generally, the inventive process is restricted to preparation of liquid soaps wherein the soap concentration does not exceed the solubility of soap in water at the neutralization temperature. More specifically, the process is suitable for the preparation of aqueous soap solutions containing 0.3% to 40%, preferably 4% to 30%, most preferably 6% to 25%, by weight of mono-, di- or triethanolamine soap.

While the disclosed process is directed particularly to the preparation of ethanolammonium soaps, it should be recognized that such process also broadly is applicable to the preparation of any liquid soaps containing sodium soap, potassium soap, ammonium soap and mixtures thereof which can be prepared by the prior art process wherein the aqueous soap is prepared by neutralizing a molten fatty acid. More particularly, it is apparent that the inventive process is suitable for preparing aqueous soaps containing sodium, potassium and/or ammonium soaps at concentrations of soap that do not exceed its solubility in water at neutralization tempertures in the range of 4° C. to 43° C. Furthermore, it appears that the process also is suitable for preparing aqueous dispersions of soap, i.e., concentrations of soap in slight excess of the solubility of soap in water at 23° C. for example, provided that such aqueous dispersions are pumpable in water at 23° C. Such concentrations vary with each particular soap, but can be ascertained readily by one skilled in the art.

As stated above in the Summary of the Invention, the inventive energy-efficient process of neutralizing a $C_{10}$–$C_{22}$ carboxylic acid with a substantially equimolar amount of a neutralizing agent to form a pumpable liquid soap comprises the steps of contacting finely divided particles of the carboxylic acid with said neutralizing agent in an aqueous medium at a temperature below the melting point of the carboxylic acid, the particle size of the acid being less than about 2000 microns and effective to form an aqueous soap which is free of visible particles of carboxylic acid, and of recovering the liquid aqueous soap solution containing from 0.3% to 40% by weight of a water-soluble soap. This process is based upon the discovery that the neutralization reaction will proceed in a timely manner if the particle size of the carboxylic acid is reduced below its threshold size. Reducing the particle size increases the surface area of the carboxylic acid and, in turn, increases the reaction rate. Thus, reducing the particle size of the carboxylic acid accomplishes essentially the same result as melting the carboxylic acid, but accomplishes the result with a savings in energy.

A significant feature of the inventive process is that the particle size of the carboxylic acid may be reduced either prior to its being contacted with the neutralizing agent or during the period it is being contacted with the neutralizing agent. Thus, the particle size of the carboxylic acid may be reduced by dry grinding and, optionally, sieving of the particulate carboxylic acid prior to its being dispersed in water and contacted with a neutralizing agent. Alternatively, the particle size of the carboxylic acid may be reduced by wet grinding after being dispersed in water such as by recycling a dispersion of carboxylic acid in water through an in-line homogenizer or mixing the aqueous dispersion using a homogenizing agitator prior to contacting the finely divided particles of carboxylic acid with the neutralizing agent. A further alternative is to subject the particles of carboxylic acid to wet grinding action while it is being contacted with the neutralizing agent. Accordingly, one skilled in the art has a great deal of flexibility in determining when and how the particle size of the carboxylic acid is to be reduced.

Although it should be recognized that the particle size of the carboxylic acid is of little or no significance where time is not a factor, i.e., where large size particles can be or are contacted with the neutralizing agent in the presence of agitation for a very long time period, it is important that the particle size of the carboxylic acid be reduced to its threshold size in a reasonably short period of time such as less than one hour, preferably less than one half hour and most preferably less than twenty minutes in order to achieve a practical industrial process. Furthermore, it should be recognized that the most important aspect of the particle size is not the average particle size, but is the size of the largest particle present. Finally, because the threshold size varies with the molecular weight of the carboxylic acid—normally decreasing as the molecular weight of the carboxylic acid increases in order to achieve neutralization in the same time period—and is affected by the presence of other ingredients, no single threshold size is applicable to the inventive process. However, the threshold size easily can be determined by one skilled in the art without undue experimentation because the threshold size corresponds to the largest particle size of carboxylic acid that will yield a neutralized soap which is free of visible particles of unreacted carboxylic acid. The presence or absence of visible unreacted carboxylic acid particles can be ascertained without difficulty for example by simply dipping a spatula into the aqueous soap and examining the soap film on the spatula for particles. Based upon limited experimentation, it appears that the threshold particle size is such that the largest particle is less than about 2000 microns because satisfactory aqueous soap was made with −10 mesh stearic acid in the presence of Ceteth 20. Aqueous soap which is free of carboxylic acid particles was made when 99% by weight of carboxylic acid was smaller than 420 microns and at least 92% by weight of said acid was smaller than 177 microns in its largest dimension. It is considered that the foregoing particle size range is consistent with experimental data using carboxylic acid within narrow sieve ranges, i.e., −40 mesh, +60 mesh; −60 mesh, +80 mesh; −80 mesh, +100 mesh (U.S. Sieve Series) which showed that lauric acid having a particle size −40 mesh, +60 mesh yielded an aqueous soap (about 19% soap) free of carboxylic acid particles after 5 minutes of mixing; whereas, the particle size of palmitic acid and stearic acid for a similar concentration of aqueous soap free of carboxylic acid particles was −80 mesh, +100 mesh of −177 microns +149 microns under the same neutralization conditions.

Another advantageous characteristic of the inventive process is that the process can be carried out in the presence of other ingredients normally found in personal care products such as shampoo, hair grooming and shave cream compositions. In fact, the presence of anionic or nonionic surfactants in the aqueous carboxylic acid dispersion at the time it is subjected to wet grinding by recycling through a homogenizer is beneficial because it reduces the grinding period required to achieve the threshold particle size and yields a carboxylic acid dispersion in water which exhibits a slower rate of separation in the absence of agitation. These improved results are believed to be due to the surface active properties provided by the detergent ingredient and similar improvement is noted when a minor proportion of neutralizing agent is present during the wet grinding operation because this material reacts with carboxylic acid to form soap which provides the surface active properties. On the other hand, similar advantages are obtained when a minor proportion of finely divided, carboxylic acid particles is incorporated in an essentially complete shampoo composition containing from 5% to 40% by weight of an anionic or nonionic detergent as the cleansing agent, optionally, a nonionic or amphoteric foam booster for the detergent, and a quantity of neutralizing agent for the carboxylic acid in order to form a minor proportion of soap in situ which functions as a conditioning agent in the shampoo. Thus, the concentration of the surfactant ingredient will be a minor proportion of the final composition which may range from 0.1% to 10%, preferably 0.5% to 7%, by weight of the resultant composition.

Similar compatibility is exhibited by this inventive process in the process of making shave cream compositions of the aerosol type and of the post-foaming gel type described in U.S. Pat. No. 3,541,581, the disclosure of which is incorporated by reference herein. More particularly, when employed in making an aerosol shave cream composition, a surfactant such as the anionic sodium lauryl sulfate or the nonionic polyoxyethylene cetyl ether may be present during the wet grinding of the carboxylic acid, e.g., palmitic acid, stearic acid or a mixture, with similar advantages and such wet grinding may either precede or take place during the neutralization of the carboxylic acid. Thereafter, any emollients or skin conditioning ingredients may be added to the aqueous soap mixture prior to its being filled into a container wherein 1 to 10 parts by weight of a normally gaseous, liquefied $C_3$–$C_4$ hydrocarbon propellant are added through the valve of the container and mixed with the aqueous soap to form an aerosol shave cream composition. Likewise, the same advantages are noted when a minor proportion of a surfactant is present during the wet grinding of the carboxylic acid in the process of preparing a post foaming gel shave cream composition such as is disclosed in U.S. Pat. No. 3,541,581 when such step is employed. Furthermore, the liquid $C_4$–$C_6$ hydrocarbon post foaming agent also can be admixed with the aqueous dispersion of carboxylic acid prior to the contacting of said carboxylic acid with the neutralizing agent to form the aqueous soap. In fact, it is preferred to introduce said $C_4$–$C_6$ liquid hydrocarbon into the aqueous carboxylic acid dispersion because a more stable homogeneous dispersion of such hydrocarbon in the resultant liquid soap is achieved and the resultant mixture is readily pumpable and easily filled into aerosol, dual compartment, dispensing containers of the bag or piston-type in liquid form rather than in gel form, with gel formation taking place within the filled container. Gelation of the resultant composition consisting essentially of, by weight, 4% to 30% of soap, 1% to 10% of post foaming agent, optionally 0.1% to 5% of cellulose polymer and the balance water, in the container can be speeded by subjecting the container to heating and agitation, two steps which are usually employed while pressure testing the filled containers for leaks of the $C_3$–$C_4$ liquified, normally gaseous hydrocarbon propellant employed to expel the composition from the container during use. Thus, the inventive liquid soap neutralization process clearly is adaptable to the process of making aqueous personal care products which contain soap as an essential component.

It should be appreciated from the foregoing discussion that an aqueous medium is an essential component in the described process and the aqueous medium will be primarily water in all cases. However, the aqueous medium may include minor proportions of organic solubilizing agents such as $C_2$–$C_3$ mono-, di and trihydric alcohols, particularly where the inventive process is employed in the preparation of cosmetic compositions which contain minor proportions, e.g., from 0.2% to 10%, preferably 0.5% to 6%, by weight of such solubilizers. In the aqueous neutralized soap the aqueous medium usually will be the balance of the composition generally 60% to 99.8%, preferably 70% to 96% and most preferably, 75% to 94%, by weight. If a mono-, di or tri hydric $C_2$–$C_4$ alcohol solubilizing agent is present in the aqueous medium, the proportion of such alcohol will range from 1% to 15%, preferably 2% to 10%, by weight of the aqueous liquid soap solution. Of course, the aqueous medium also will constitute the balance of the aqueous cosmetic compositions containing soap produced using the inventive process, with the proportion of said aqueous medium varying with the particular product and the proportion of solubilizing alcohol therein being essentially the same as in said aqueous liquid soap solution.

The inventive process is further illustrated by the following Examples wherein the proportions are set forth on a weight basis. Furthermore, unless otherwise specified, all proportions set forth elsewhere in the specification and claims are on a weight basis.

EXAMPLE 1

A preferred process of making a liquid triethanolamine soap without application of external heat comprises forming a dispersion of 20% by weight of palmitic acid in water at a temperature of 22° C. by adding particulate palmitic acid to water in a vessel agitated by a turbine. The particle size distribution (U.S. Sieve Series) of the particulate palmitic acid on a weight basis is:

+40 mesh (420 micron sieve opening)—94.4%;
−40, +60 mesh (250 micron sieve opening)—2.7%;
−60, +100 mesh (149 micron sieve opening)—2.0%;
−100, +325 mesh (44 micron sieve opening)—0.9%.

The particle size of the dispersed palmitic acid is reduced by wet grinding by recycling the aqueous dispersion from the agitated tank through a Tekmar SD-40 homogenizer at a 0.1 setting (0.1 mm opening on the stator slot) for a period of fifteen minutes. The aqueous dispersion is checked for particles by pouring a weighed sample through a 40 mesh sieve and no particles are noted.

The aqueous dispersion of the wet ground palmitic acid is neutralized by adding 47.414 parts by weight of the dispersion to 52.586 parts by weight of a mixture of 10.49% by weight of triethanolamine in water which is being stirred using a turbine agitator. Agitation is continued for about two minutes after all of the aqueous fatty acid dispersion is added. The resultant liquid contains 15% by weight of triethanolamine palmitate and when a sample of the liquid soap is poured through a 40 mesh screen (U.S. Sieve Series), no particles are noted on said screen.

The resultant liquid soap is then recycled through the Tekmar homogenizer using a 1 setting (1 mm slot opening), with samples being taken after 2, 5, 10, 20, 30 and 60 minutes. Again, no particles are noted when the two minute and five minute recycle samples of the liquid soap are poured through a 40 mesh screen (U.S. Sieve Series). The viscosity of the various samples at 26.7° C. is set forth in Table I below based upon measurements taken after ninety seconds using a Brookfield HATD Viscometer, spindle #4 rotating at 20 rpm. For purposes of comparison, the viscosity of an aqueous soap containing 15% by weight of triethanolamine palmitate that was produced by neutralizing a dispersion of melted palmitic acid in water at 71° C. with a 40% weight concentration of triethanolamine in water—a typical standard neutralization process—is included in Table I.

TABLE I

| Sample | Viscosity (cps.) |
| --- | --- |
| Comparative | 1380 |
| 2′ Recycle | 1060 |
| 5′ Recycle | 960 |
| 10′ Recycle | 960 |
| 20′ Recycle | 960 |
| 30′ Recycle | 1120 |
| 60′ Recycle | 1020 |

Table I shows that triethanolamine palmitate prepared by the inventive process has a slightly lower viscosity than the typical process which is carried out at about 71° C. However, since all of the samples in Example 1 except the comparative are slightly aerated, part of the difference in viscosity may be due to such aeration.

EXAMPLE 2

The process of Example 1 is repeated with the exceptions that the concentration of palmitic acid is increased from 20% by weight to 24% by weight in the aqueous dispersion which is subjected to wet grinding by recycling through the Tekmar SD-40 at 0.1 setting; the concentration of the triethanolamine neutralizing solution is increased from 10.49% by weight to 13.8% by weight; and the neutralization is carried out using a turbine agitator. The resultant liquid soap contains 19% by weight of triethanolamine palmitate and this liquid soap is recycled through the Tekmar homogenizer for periods of 1′, 6′ and 16′ to determine the effect of shearing on the viscosity of the final liquid soap, with said viscosity measurements being made under the same conditions as set forth in Example 1. The results are set forth in Table II.

TABLE II

| Sample | Viscosity (cps.) |
| --- | --- |
| Soap-no shear | 9080 |
| Soap-1′ shear | 5560 |
| Soap-6′ shear | 3160 |
| Soap-16′ shear | 3720 |

Table II shows that added shear does reduce the viscosity of the liquid soap produced by the inventive process and, thus, part of the reduction in viscosity noted in Table I above must be due to the additional shear which is employed in the inventive process.

EXAMPLE 3

A dispersion of 20% by weight of palmitic acid is prepared by dispersing the particulate fatty acid used in Example 1 in water at a temperature of 25° C. using turbine agitation. Samples of the resultant aqueous dispersion are subjected to wet grinding by recycle through the Tekmar SD-40 homogenizer at a setting of 1.0 (1 mm slot opening) for varying periods of time from 2 minutes to 60 minutes and then are poured through a set of screens of varying sizes—40 mesh, 60 mesh, 100 mesh and pan (U.S. Sieve Series)—to determine the particle size of each sample which is set forth in Table III below.

TABLE III

| Grinding Time | +40 mesh | Weight Percent (%) | | |
| --- | --- | --- | --- | --- |
| | | −40, +60 mesh | −60, +100 mesh | −100 mesh |
| 0 | 94.4 | 2.6 | 2.0 | 1 |
| 2 | 12.9 | 18.7 | 14.1 | 55.3 |
| 10 | 2.7 | 14.4 | 13.3 | 69.6 |
| 20 | 1 | 6 | 2.1 | 90.9 |

The samples in Table III are mixed for one to two minutes with an equimolar concentration of aqueous triethanolamine at 26° C. to form a liquid soap containing 15% by weight of triethanolamine palmitate using turbine agitation. Samples of the resulting soap solutions are visually checked for unreacted particles of fatty acid in order to obtain a correlation between particle size and reaction completion, with the results being shown in Table IV below.

TABLE IV

| Fatty Acid Grinding Time | Visual Inspection Result |
| --- | --- |
| 0 | Many large particles |
| 2 | Many smaller particles |
| 5 | Fewer small particles |
| 10 | Very few, very small particles |
| 20 | No particles |
| 30 | No particles |
| 60 | No particles |

The foregoing experiments clearly demonstrate that the critcial factor affecting neutralization is not the average or mean particle size, but is the quantity of large particles or, conversely, the quantity of particles below a critical size—the threshold size—that is important. Thus, for palmitic acid the threshold size is 99% by weight less than 40 mesh, i.e., less than 420 microns, and about 92% by weight less than 80 mesh, i.e., 177 miployed a 50% weight concentration of sodium hydroxide in water as the neutralizing agent.) Comparative aqueous soap solutions made by high temperature neutralization also are included in Table V.

TABLE V

| Formula | Acid Mesh Size | Neutralization temperature (°C.) | Visual Description |
|---|---|---|---|
| Lauric acid —50 gm; Triethanolamine —37.2 gm | −40, +60 | 26.7° C. | Clear solution w/no particles |
| Lauric acid —50 gm; Triethanolamine —37.2 gm | −60, +80 | 26.7° C. | Clear solution w/no particles |
| Lauric acid —50 gm; Triethanolamine —37.2 gm | −80, +100 | 26.7° C. | Clear solution w/no particles |
| Lauric acid —50 gm; Triethanolamine —37.2 gm | Liquid | 66° C. | Clear solution |
| Palmitic acid —50 gm Triethanolamine —29.1 gm | −40, +60 | 26.7° C. | Cloudy solution, some particles |
| Palmitic acid —50 gm Triethanolamine —29.1 gm | −60, +80 | 26.7° C. | Cloudy solution, some particles |
| Palmitic acid —50 gm Triethanolamine —29.1 gm | −80, +100 | 26.7° C. | Cloudy solution, no particles |
| Palmitic acid —50 gm Triethanolamine —29.1 gm | Liquid | 77° C. | Cloudy solution |
| Stearic acid —50 gm Triethanolamine —26.2 gm | −40, +60 | 26.7° C. | Cloudy solution, some particles |
| Stearic acid —50 gm Triethanolamine —26.2 gm | −60, +80 | 26.7° C. | Cloudy solution, some particles |
| Stearic acid —50 gm Triethanolamine —26.2 gm | −80, +100 | 26.7° C. | Cloudy solution |
| Palmitic acid —45 gm; Stearic acid —12.5 gm; Triethanolamine 32.6 gm | −40, +60 | 26.7° C. | Cloudy solution, some particles |
| Palmitic acid —45 gm; Stearic acid —12.5 gm; Triethanolamine 32.6 gm | −60, +80 | 26.7° C. | Cloudy solution, some particles |
| Palmitic acid —45 gm; Stearic acid —12.5 gm; Triethanolamine 32.6 gm | −80, +100 | 26.7° C. | Cloudy solution |
| Palmitic acid —45 gm; Stearic acid —12.5 gm; Triethanolamine 32.6 gm | Liquid | 77° C. | Cloudy solution |
| Lauric acid 50 gm; 50% NaOH—20 gm | −80, +100 | 26.7° C. | Reacted and formed hard lumps, solid following day |
| Stearic acid —50 gm; 50% sodium hydroxide —14.1 gm | −80, +100 | 26.7° C. | No reaction | crons.

EXAMPLE 5

Since the threshold particle size could be expected to be different for individual fatty acids, lauric, palmitic and stearic acid are dry ground using a Stokes granulator and are separated into the following particle size fractions (U.S. Sieve Series): −40, +60 mesh (−420, +250 microns); −60, +80 mesh (−250, +177 microns); −80, +100 mesh (−177, +149 microns) and −100 mesh (−149 microns). Laboratory batches are prepared by forming 500 gram aqueous dispersions containing 10% by weight of acid in water at 26° C. in a 600 ml beaker using an electric laboratory mixer with a turbine impeller. Mixing is continued for five minutes. Triethanolamine then is added in an equimolar amount while continuing the turbine agitation at 26° C. for another five minutes and the resultant aqueous soap solution is visually checked using a microscope for particles to determine the completeness of the neutralization reaction. The results of these evaluations are shown in Table V. Results also are shown in Table V for neutralization of an aqueous dispersion containing 9% by weight of palmitic acid and 2.5% by weight of stearic acid as well as for neutralization with an equimolar amount of sodium hydroxide substituted for triethanolamine. (Neutralization with sodium hydroxide em- The results in Table V confirm that the critical particle size of the fatty acid is different for each of the listed acids, with the critical size decreasing as the molecular weight of the acid increases. However, the results do not indicate the critical particle size for lauric acid because all particles having a size of 470 microns or less reacted with triethanolamine immediately. On the other hand, the maximum particle size for both palmitic acid, stearic acid and mixtures thereof is −177 microns (−80 mesh). Furthermore, the foregoing results using particles obtained by dry grinding appear to be consistent with the results observed on particles obtained by wet grinding based upon the actual results for palmitic acid. For example, complete neutralization is obtained when 7% of the particles obtained by wet grinding were larger than 250 microns and 91% were smaller than 149 microns; whereas, complete neutralization is obtained when all of the particles produced by dry grinding are in the range of 149 microns to 177 microns.

Table V also confirms that the inventive process—neutralization at 4° C. to 43° C.—is not satisfactory for the preparation of aqueous liquid soaps containing 11.1% by weight of sodium laurate. It is believed that the unsuccessful result is due to the fact that this concentration of sodium laurate exceeds its solubility in water at 25° C. by about 455%. The same rationale also explains the lack of saponification of stearic acid because 10.7% calculated sodium stearate concentration is more than 10,000% greater than the solubility of sodium stearate in water at 25° C.

EXAMPLE 6

The process of Example 3 is repeated with the exception that the concentration of palmitic acid in the aqueous fatty acid dispersion is increased to 15% by weight and said fatty acid is dispersed in water at a temperature of 20° C. using a turbine agitator. Mixing is continued for about 5 minutes after all of the palmitic acid has been added. Thereafter, the dispersion is recycled through the Tekmar SD 40 homogenizer at a setting of 0.1 (0.1 mm slot opening) for twenty minutes. Visual inspection of the resultant dispersion which is somewhat aerated shows no visible particles. An equivalent weight of triethanolamine (8.73 parts by weight) is added to the palmitic acid dispersion which is agitated by a turbine mixer at a temperature of about 24° C. and mixing is continued for five minutes after the neutralizing agent is added. The resultant cloudy liquid contains about 21.8% by weight of triethanolamine palmitate.

The energy savings resulting from the inventive neutralization process wherein no external heat is applied can be approximated using the heat capacity of water for the range of temperatures according to the following equation:

$$\Delta H = a T + \tfrac{1}{2} (b \times 10^{-3}) T^2 + \tfrac{1}{3} (c \times 10^{-6}) T^3 - \frac{d \times 10^5}{T} - A$$

wherein the constants for water are:
 a = 8.2 cal/mole
 b = 0.4 cal/mole
 c = 0.0 cal/mole
 d = 0.2 cal/mole
 A = 49.67 kcal/mole
 T start = 298° K.

Assuming that the batch temperature in a normal heating process must be raised to 74° C., the resulting heat capacity calculates to be 159.6 kilocalories (kcal) per kilogram (kg). Thus, applying this value to the preparation of a 14.763 kg batch of soap solution wherein the mixture of water and fatty acid is heated to 74° C., neutralized at that temperature and cooled to 25° C. results in 4346.8 kcal of energy required to produce said batch—1990.6 kcal for heating and 2356.2 kcal for cooling. On the other hand, the energy consumed in producing the same batch by wet grinding using the 1.5 hp Tekmar SD-40 mill for twenty minutes is 320.7 kcal—1.5 hp × 10.69 kcal/min × 20 minutes. Accordingly, the inventive process achieves significant energy savings over the standard heating process employed in neutralizing $C_{12}$-$C_{18}$ fatty acids to form the corresponding soap.

EXAMPLE 7

The inventive process is particularly useful in preparing an aerosol shave cream having the following composition:

|  | % by weight |
|---|---|
| Part I |  |
| Triethanolamine stearate | 11.0 |
| Sodium lauryl sulfate | 1.8 |
| Polyethylene glycol ether of cetyl alcohol (20 EO).Ceteth 20 | 3.0 |
| Blue color solution | .02 |
| Perfume | .6 |
| Water | q.s. |
|  | 100.0 |
| Part II |  |
| Part I | 96.5 |
| Propane/isobutane (20:80 weight ratio) | 3.5 |
| Total | 100.0 |

This composition is prepared by dispersing 3 parts by weight of molten Ceteth 20 in 61.8 parts by weight of water at a temperature of 21° C. Thereafter, an aqueous mixture of 3.57 parts by weight of triethanolamine, 0.02 parts by weight of blue color solution and 21.78 parts by weight water is added to the foregoing aqueous mixture at a temperature of about 21° C. while agitating the mixture with an Eppenbach laboratory homogenizer set at a speed to minimize aeration. 7.43 parts by weight stearic acid flakes having a particle size such that 100% by weight is less than 10 mesh, less than 2000 microns, is dispersed in the water containing the Ceteth 20 and triethanolamine at a temperature of about 21° C. and while agitating the mixture using a Eppenbach laboratory homogenizer set at a speed to minimize aeration. Agitation is continued for fifteen minutes and thereafter 1.8 parts by weight of sodium lauryl sulfate and 0.6 parts by weight of perfume are added to the aqueous fatty acid dispersion in the presence of moderate agitation using the Eppenbach homogenizer. Agitation is continued for about ten minutes and 96 parts by weight of the resultant homogeneous mixture is filled into an aerosol container which is closed by crimping on a valve. The mixture of propane and isobutane is added to the container as a liquid under pressure through the valve and the container is agitated to yield a substantially homogeneous aerosol shave cream composition within the container.

The foregoing process is very energy efficient because it employs particulate stearic acid, thereby avoiding the step of melting said acid. Further, the entire process is conducted without either external heating or cooling, and the neutralization reaction takes place simultaneously with the reduction of the particle size of the stearic acid by the homogenizer mixer. Additionally, the processing time required to make this product is significantly reduced as compared with the usual process wherein the stearic acid is melted and dispersed in water at a temperature of 65° C. and this mixture is cooled to about 30° C. in the course of making Part I of the shave cream composition.

EXAMPLE 8

The following aerosol shave cream composition also is prepared using a variation of the process described in Example 7 above.

|  | % by weight |
|---|---|
| Part I |  |
| Mixed sodium potassium stearate (4/1 mole ratio of potassium to sodium | 8.06 |
| Mixed sodium/potassium cocoate (4/1 mole ratio of potassium to sodium) | 1.14 |
| Glycerine | 2.7 |

-continued

|  | % by weight |
|---|---|
| Lauric-myristic diethanolamide | 1.0 |
| Color solution | 0.25 |
| Perfume | 0.6 |
| Water | q.s. |
|  | 100.00 |
| Part II |  |
| Part I | 96.5 |
| Propane/Isobutane (20:80 weight ratio) | 3.5 |
|  | 100.0 |

This composition is prepared using a variation of the process set forth in Example 7. More specifically, 7.16 parts by weight of −20 mesh stearic acid, 2.7 parts by weight of glycerine, 1 part by weight coconut oil fatty acids and 1 part by weight of lauric myristic diethanolamide are weighed into a beaker containing 62.9 parts by weight of water at 21° C. and this mixture is agitated with a laboratory Lightning mixer—a propeller-type mixer—to form an aqueous dispersion of the described ingredients. Thereafter, 24.38 parts by weight of an aqueous solution containing 5.6% by weight of potassium hydroxide and 1% by weight of sodium hydroxide at 21° C. is added to the agitating aqueous dispersion and mixing is continued for approximately one hour to form a homogeneous aqueous soap mixture. 0.6 parts by weight of perfume are added during the mixing period and the resultant product is filled into an aerosol container and treated in the same manner described in Example 7 to yield a satisfactory aerosol shave cream product.

The foregoing example again demonstrates simultaneous neutralization and reduction of particle size of the stearic acid. Further, it shows the use of the inventive process to form a mixed potassium-sodium stearate-cocoate soap containing 9.2% by weight of soap.

EXAMPLE 9

The inventive process also has utility in making a post-foaming gel shave cream by admixing 0.35 parts by weight of triethanolamine with 57.15 parts by weight of water at 25° C. in a mixing vessel agitated by a turbine and thereafter dispersing 9 parts by weight of palmitic acid particles (−20 mesh) and 2.5 parts by weight of stearic acid particles (−20 mesh) in said mixture. The particle size of the dispersed fatty acids is reduced by recycle through a colloid mill having a setting of 180 microns. Thereafter, 1.78 parts by weight of a gum solution is prepared by wetting a particulate mixture of hydroxyethyl cellulose and hydroxypropyl cellulose with a sorbitol solution containing 70% by weight of sorbitol and dispersing said mixture in 21.97 parts by weight of water using turbine agitation to form a liquid containing 1.17% by weight of the cellulose mixture. The aqueous cellulose mixture and a mixture of perfume and a glyceryl fatty acid ester, e.g., glyceryl isostearate, are admixed with the aqueous fatty acid dispersion in a mixing vessel agitated by a turbine. 93.5 parts by weight of the foregoing aqueous fatty acid/perfume-fatty acid ester/cellulose dispersion which contains about 12.3% by weight of fatty acid is mixed with 2.3 parts by weight of a mixture of isopentane and isobutane using an in-line static mixer and an air powered dynamic mixer in tandem maintained under a pressure of about 80 psig and this dispersion at 23° C. is neutralized with 6.43 parts by weight of the mixture of 6.35 parts by weight of triethanolamine and 0.08 parts by weight of color solution to form a liquid triethanolamine soap solution at 23° C. without the addition of external heat. The resultant thin mixture is filled through the valve into the inner bag of a "bag in can" or seprotype container using a product dosing apparatus. Some of the containers are placed in a 43° C. heated chamber for an hour or in a 50° C. water bath for about ten minutes and gels showing acceptable consumer characteristics are formed in heated containers. The contents of unheated cans maintained as a control are very thin and do not form an acceptable gel product within the same time period.

The process of Example 9 also can be carried out to make satisfactory post-foaming gel shave cream compositions which do not contain any water-soluble cellulose gelling agents. Furthermore, satisfactory post-foaming gel compositions can be prepared using pressures in the range of 10 to 100 psig on the aqueous mixture of particulate fatty acid and post-foaming agent at temperatures in the range of 4° C. to 43° C.

We claim:

1. A process of neutralizing $C_{10}$–$C_{22}$ mono-carboxylic acids with a substantially equimolar amount of a neutralizing agent to form a pumpable, liquid soap containing from 0.3% to about 40% by weight of a water-soluble soap dissolved in water which comprises the step of contacting finely divided particles of said $C_{10}$–$C_{22}$ carboxylic acid in an aqueous medium with said neutralizing agent at a temperature from 40° C. to 43° C. and below the melting point of said fatty acid, said particles of carboxylic acid having a size less than about 2000 microns which is effective to form a liquid soap free of carboxylic acid particles, and recovering said pumpable, liquid soap solution.

2. A process according to claim 1 wherein said monocarboxylic acid contains 12 to 18 carbon atoms.

3. A process according to claim 2 wherein an aqueous dispersion of finely divided particles of said carboxylic acid is formed in water at a temperature of from 4° to 43° C., said carboxylic acid having a particle size such that about 99% by weight is less than 420 microns in its largest dimension and about 92% by weight is less than 177 microns in its largest dimension, and said aqueous dispersion is reacted with said neutralizing agent.

4. A process according to claim 2 wherein said aqueous dispersion of finely divided particles of carboxylic acid is formed by dispersing particulate carboxylic acid obtained by dry grinding and/or sieving in water.

5. A process according to claim 2 wherein said aqueous dispersion of finely divided particles of carboxylic acid is formed by wet grinding a dispersion of particulate carboxylic acid in water.

6. A process according to claim 1 wherein said particles of carboxylic acid are reduced in particle size by wet grinding while simultaneously contacting said particles with said neutralizing agent.

7. A process according to claim 2 wherein said neutralizing agent is selected from the group consisting of mono-, di- and triethanolamine.

8. A process according to claim 7 wherein said neutralization is at a temperature of from 21° C. to 32° C.

9. A process according to claim 7 wherein said aqueous dispersion of carboxylic acid contains from 4% to 25% by weight of carboxylic acid.

10. A process according to claim 1 wherein an aqueous dispersion of finely divided particles of carboxylic acid is formed in the presence of a minor proportion of a water-soluble surfactant.

11. A process according to claim 9 wherein said water soluble surfactant is a water soluble mono-, di- or triethanolamine soap.

12. A process according to claim 1 wherein said pumpable, liquid soap solution contains from 4% to 30% by weight of water-soluble soap and 90 to 99 parts by weight of said soap is admixed with from 1 to 10 parts by weight of a normally gaseous, liquid $C_3$–$C_4$ hydrocarbon in a valved, container to form an aerosol shave cream composition.

13. A process according to claim 11 wherein said soap is a mono-, di- or triethanolammonium soap of a $C_{12}$ to $C_{18}$ carboxylic acid.

14. A process according to claim 11 wherein said aqueous dispersion is admixed with a liquid $C_4$–$C_6$ hydrocarbon post-foaming agent at a temperature of from 4° C. to 43+ C. and a pressure of from 10 to 100 psig prior to being contacted with said neutralizing agent and the resultant pumpable, liquid soap composition is filled into the upper compartment of a valved container having a normally gaseous liquefied $C_3$–$C_4$ hydrocarbon propellant in the lower compartment and said container is heated at a temperature of from 45° C. to 70° C. and shaken to form a post-foaming gel shaving cream consisting essentially of by weight, 4% to 30% of soap, 1% to 10% of post-foaming agent and the balance water.

15. A process according to claim 11 wherein an aqueous dispersion of finely divided particles of said carboxylic acid is formed in water at a temperature of from 4° C. to 43° C. said carboxylic acid having a particle size such that about 99% by weight is less than 420 microns in its largest dimension and about 92% by weight is less than about 177 microns in its largest dimension.

16. A process according to claim 11 wherein said aqueous dispersion of finely divided particles of carboxylic acid is formed by dispersing particulate carboxylic obtained by dry grinding and sieving in water.

17. A process according to claim 11 wherein said aqueous dispersion of finely divided particles of carboxylic acid is formed by wet grinding a dispersion of particulate carboxylic acid in water.

18. A process according to claim 11 wherein said neutralizing agent is mono-, di- or triethanolamine.

19. A process according to claim 11 wherein an aqueous mixture of sorbitol and a cellulose polymer selected from the group consisting of hydroxyethyl cellulose, hydroxypropyl-cellulose and mixture thereof is admixed with said aqueous carboxylic acid dispersion prior to its admixture with said liquid $C_4$–$C_6$ hydrocarbon post-foaming agent.

* * * * *